United States Patent [19]

Weinstein et al.

[11] 4,243,046
[45] Jan. 6, 1981

[54] V LEAD EXTENDER FOR ECG

[75] Inventors: Belson J. Weinstein, Palo Alto; Bruce H. Hyndman, Newark, both of Calif.

[73] Assignee: Belson J. Weinstein, Palo Alto, Calif.

[21] Appl. No.: 63,841

[22] Filed: Aug. 6, 1979

[51] Int. Cl.³ .............................................. A61B 5/04
[52] U.S. Cl. .................................................. 128/709
[58] Field of Search ............... 128/639, 644, 695, 696, 128/709, 710, 902

[56] References Cited

U.S. PATENT DOCUMENTS

| | | | |
|---|---|---|---|
| 2,400,583 | 5/1946 | White | 128/709 |
| 2,647,508 | 8/1953 | Pelavin | 128/709 |
| 3,058,458 | 10/1962 | Daneman | 128/709 |
| 3,631,851 | 1/1972 | Hesen | 128/696 |
| 3,757,778 | 9/1973 | Graham | 128/696 |
| 3,868,948 | 3/1975 | Graetz | 128/709 |
| 3,991,747 | 11/1976 | Stanly et al. | 128/709 |

*Primary Examiner*—William E. Kamm
*Attorney, Agent, or Firm*—Julian Caplan

[57] ABSTRACT

An auxiliary rotary selector switch is provided, preferably conveniently near a standard single-channel ECG instrument. The V lead of the instrument is connected to one end of the center conductor of a coaxial cable, the opposite end of which is connected to the center contact of the auxiliary switch. Each of several stationary switch contacts is connected to a conductor of an auxiliary patient cable, the opposite ends of the conductor being attached to a corresponding number of V electrodes spaced across the chest of the patient. By oscillating the center contact, separate V readings, one for each of the chest electrodes may be recorded. The extender is actually connected to the ECG instrument when the selector switch of that instrument is turned to the V lead position, and the signals from the plural V electrodes are recorded serially on the chart as the auxiliary selector switch is turned.

5 Claims, 2 Drawing Figures

V LEAD EXTENDER FOR ECG

This invention relates to a new and improved V lead extender for ECG instruments.

It is desirable to obtain ECG readings using the so-called "V" lead of the instrument from electrodes attached to the chest of the patient from three to six locations accurately spaced across the chest. Heretofore, there have been several alternatives whereby such readings may be obtained.

The most recent means for obtaining plural V lead readings has been the three channel ECG instrument which simultaneously records readings from three sources. Such machines, however, are expensive. Further, many single channel machines are in the field. A feature of the present invention is the fact that it may be connected into a single channel machine either as a retro-fit or as original equipment.

A second alternate available heretofore is to attach the electrode to the skin at the various positions across the chest serially. This is time consuming in the sense that the ECG examination is in progress while the relocation of the electrode is taking place. This is particularly undersirable during stress tests, such as treadmill tests. It is understood that the use of the invention is not limited to such tests.

Still another alternative for obtaining plural V lead readings is initially to attach plural electrodes across the chest of the patient and then to move the clip of the V lead to each of the electrodes in turn. This alternative requires manipulation of the clip of the V lead during the examination, and such manipulation may be awkward during stress tests.

The present invention is used as an attachment to a standard single-channel ECG instrument. Plural electrodes are attached across the chest prior to the examination, and auxiliary V leads are secured to these electrodes prior to commencement of the examination and remain in position until completion of the examination. Thus, it is not necessary during the course of the examination to relocate the electrode or to move the clip of a single V lead from electrode to electrode while the examination is taking place.

A feature of the invention is the fact that an inexpensive rotary selector switch is located near the standard ECG instrument. When the instrument is adjusted for V lead readings, the technician moves the auxiliary selector switch from position to position to obtain readings at several electrodes distributed across the chest of the patient.

A further feature of the invention is the fact that very little alteration of the internal circuitry of the standard machine is required. Two wires leading from the auxiliary selector switch are attached into the wiring of the ECG machine to provide a floating ground at the required intervals, and to impose upon the stylus the appropriate movement to make a chart for each of the auxiliary V leads.

A still further feature of the invention is the fact that its operation is extremely simple and requires very little additional education of the technician using the same.

The principal purpose of the invention, of course, is to improve diagnostic accuracy of coronary artery disease and other heart conditions either during various stress tests or other electrocardiogram tests.

Other objects of the present invention will become apparent upon reading the following specification and referring to the accompanying drawings in which similar characters of reference represent corresponding parts in each of the several views.

There are a variety of single-channel ECG instruments presently in use. For convenience, the present invention is shown as an auxiliary to a Hewlett-Packard Company Model 1500B. It will be understood that the present invention may be used with other instruments.

Figure 1:
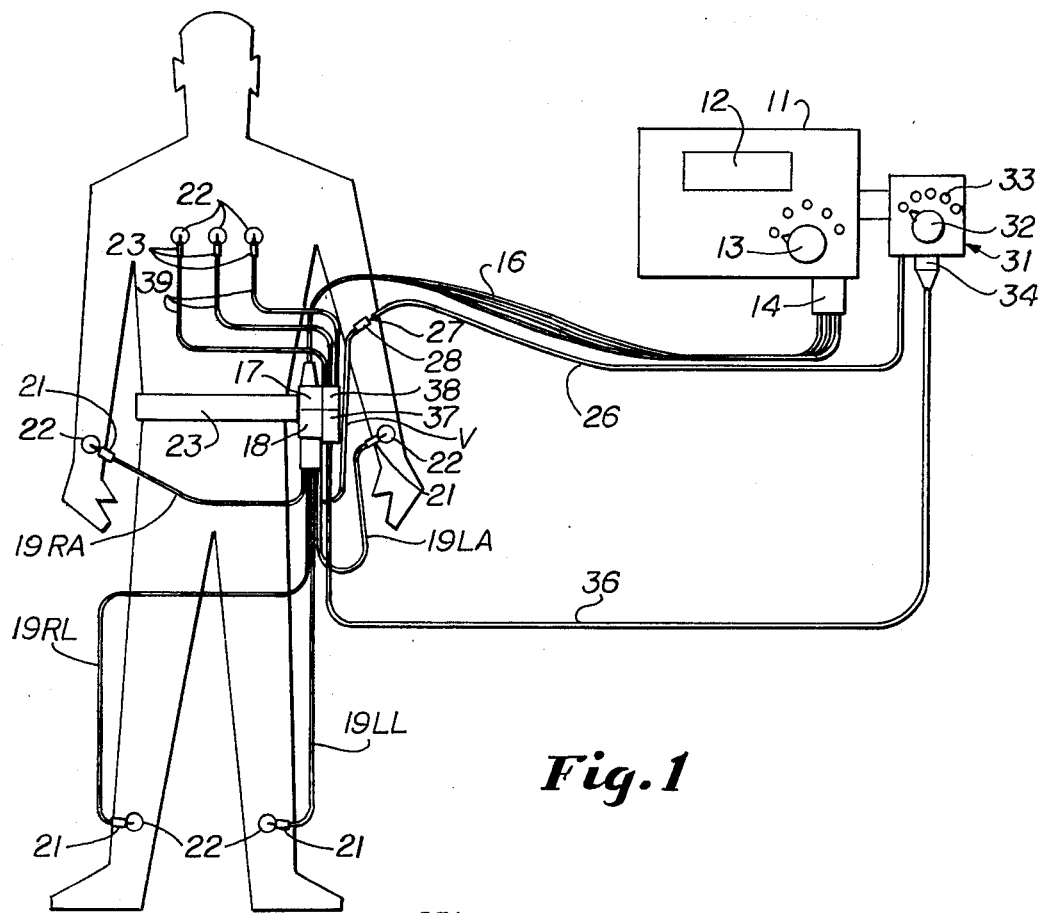
FIG. 1 is a schematic view showing a standard single-channel ECG instrument and the apparatus of the present invention and showing the connection on the main patient cable from the ECG to electrodes distributed at locations on the body of the patient as well as the auxiliary or extended V leads of the present invention connected to locations across the chest.

The instrument 11 is shown schematically in FIG. 1. Such an instrument has a chart window 12 across which chart paper is driven. A stylus (not shown) moved by a galvanometer (also not shown) marks the chart paper with the well-known characteristic ECG readings used in diagnosis of heart conditions. In such standard machines, readings are obtained by connection of internal circuitry of the instrument 11 to selected locations on the body of the patient. Thus, the standard machine 11 has a rotary switch knob 13 which selects the various combinations of electrode position readings to be recorded.

Plug 14 at one end of the main patient multi-strand cable 16 is connected to instrument 11. The distal of cable 16 is conventionally provided with a plug 17 which connects to a second plug 18. From the plug 18 extend the various individual cables 19, the outer ends of which are provided with clips 21 which attach to electrodes 22 fitted to the body of the patient at appropriate locations prior to commencement of the examination. As shown in FIG. 1, there are electrodes 22 at locations RA (right arm), RL (right leg), LA (left arm) and LL (left leg). To facilitate attachment of the electrodes prior to the examination, particularly during stress tests, a belt 23 is fixed around the waist of the patient and the plug 18 is clipped thereto.

As has heretofore been explained, at least one V lead electrode 22 is always attached to the chest of the patient adjacent the heart. It is desirable that up to six locations spread across the chest at scientifically determined loci be used. In accordance with the present invention, these electrodes are connected into the instrument 11 serially. Although in the drawings and in the following description three auxiliary V leads are disclosed, it will be evident to one skilled in this art that a lesser or greater number of leads may be used.

A coaxial cable 26 is provided. The center conductor 27 of cable 26 is electrically connected to the standard V lead which extends from plug 18. A means of connection is to solder the clip 28 to the V lead to conductor 27. The opposite end of the center conductor 27 is connected into the auxiliary switch of the present invention, and the shield is grounded at the instrument end.

Auxiliary rotary selector switch 31 is preferably located conveniently near the instrument 11. Externally such switch 31 has a rotary selector knob 32 and a plurality of stationary contact indicators 33. Its internal construction is hereinafter described. Plug 34 of auxiliary patient cable 36 is plugged into the switch 31. Cable 36 is here shown to comprise three conductors because there are three electrodes 22 distributed across the chest of the patient. It will be understood, however, that more or less conductors could be used depending upon the number of the lead positions desired. At the distal end of cable 36 is a first plug 37 which is plugged into plug 38, preferably supported by belt 23. Leading from plug 38 are three V leads 39 which are clipped by clips 23 to the electrodes 22 across the chest of the patient.

Figure 2:
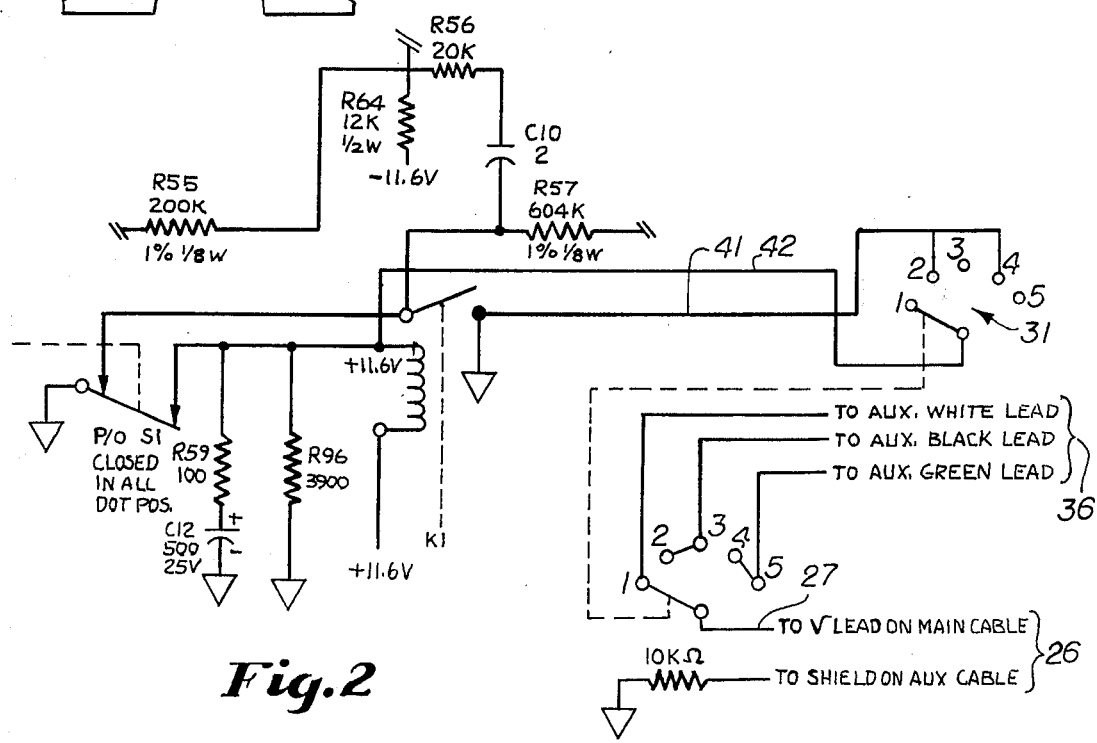
FIG. 2 is a schematic wiring diagram of the auxiliary switch of the present invention and a portion of the circuitry of a standard single-channel ECG machine.

Directing attention now to the schematic wiring diagram FIG. 2, it will be seen that the switch 31 is a two-deck switch. Center conductor 27 of cable 26 is connected to the center or movable contact of the lower deck while the shield of cable 26 is connected to ground through a 10 Kohm resistor to provide a floating ground. There are five contacts on the lower deck of switch 31. The first two are shunted and connected to one of the leads of the cable 36. The third and fourth contacts are also shunted and connected to another lead of cable 36, while the fifth contact is connected to the third lead of cable 36.

The movable contact of the upper deck of switch 31 is mechanically connected to the center contact of the lower deck. The center contact of the upper deck is connected by a wire 41 to a source of positive DC voltage in the instrument 11, here shown to be plus 11.6 volts. For purpose of explanation, a wire 42 is attached at one end to the junction of components R96 and R59 as shown at page 6–23 of the Hewlett-Packard Service Manual of the Model 1500B.

As illustrated in FIG. 2, the arrangement of wires of the switch contacts and mechanical stops results in the following action:

| Position | Action |
| --- | --- |
| 1. | "Internal" wires disconnected, V lead connected to a first auxiliary V lead. |
| 2. | "Internal" wires connected, V lead connected to a second auxiliary V patient cable. |
| 3. | "Internal" wires disconnected, V lead connected to a second auxiliary V patient cable. |
| 4. | "Internal" wires connected, V lead connected to third auxiliary V patient cable. |
| 5. | "Internal" wires disconnected, V lead connected to the third auxiliary patient lead. |

The net result of this arrangement is that when the selector switch 13 of instrument 11 is set for the "V" position, selection of three, rather than one, V leads is possible. In this operating configuration, rotation of the auxiliary switch knob 32 from position 1–5 mimics the action of the lead selector switch of the Model 1500B instrument 11, alternately selecting one of three auxiliary input leads or zeroing the chart stylus. The latter action is accomplished by causing a circuit connection in the Model 1500B identical to that made when the lead selection switch 13 is rotated to a "dotted" position.

In use of the device, in addition to the standard arm and leg electrode placement, three electrodes 22 are affixed to the chest of the patient (it being understood that more or less such electrodes may be employed with modification of the device as would readily occur to one skilled in the art). The standard leads 19 are connected to the arm and leg electrodes while the auxiliary V leads 39 are connected to the chest electrodes 22. The plugs 18 and 38 are preferably supported by the belt 23 which is attached and the plugs 17 and 37 are connected to the plugs 18 and 38, respectively. By technician manipulation of the selector knob 13, a conventional electro-cardiograph is obtained through the use of the instrument 11, except that when the knob 13 is turned to the V position, the technician the turns the knob 32 serially to the five positions 33 of the switch 31. Thus, three different V charts may be obtained.

What is claimed is:

1. Apparatus for extending the V lead of an ECG instrument of the single channel type having a driven chart, a stylus for marking characteristic electrocardiographs on said chart, a plurality of lead wires connected to said instrument, including a single "V" lead, means for attaching the distal of at least some of said leads to the skin of a patient, electrical means for supplying voltage to said leads and also for driving said stylus and a first selector switch for serially connecting said leads to said instrument, said first switch having a "V" position connecting said "V" lead to said instrument, the improvement which comprises a conductor, means for connecting said V lead to said conductor, a second selector switch having a movable central contact connected to said conductor and a plurality of stationary contacts, a plurality of auxiliary patient leads, each said auxiliary lead being connected at a first end to one of said stationary contacts and at its distal to second means for attachment to the skin of said patient at a plurality of V positions, whereby when said instrument first selector switch is at "V" position, by serially turning said movable central contact readings at each of said plurality of V positions may be obtained on said chart.

2. Apparatus according to claim 1 in which said conductor is the central wire of a coaxial cable which has a shield and in which said instrument has a floating ground, said shield being connected to said floating ground.

3. Apparatus according to claim 2 in which said second selector switch has a second deck having a second movable contact connected to move with said first-mentioned movable contact and a second set of a plurality of second stationary contacts consisting of dummy contacts unconnected to any element other than said second movable contact and active stationary contacts, said active contacts being connected to said floating ground, said second movable contact being connected to a source of DC power in said instrument, whereby, when said first movable contact is not connected to one of said first-mentioned stationary contacts, said source of power is connected to said floating ground.

4. Apparatus according to claim 1 whereby said auxiliary patient leads consist of a first section comprising a multi-conductor cord and a first plug member and a second section comprising a second plug member engageable with said first plug member and a plurality of leads extending from said second plug member.

5. Apparatus according to claim 4 which further comprises a belt to encircle to waist of the patient and means to support said second plug member from said belt.

* * * * *